(12) United States Patent
Erickson et al.

(10) Patent No.: US 10,799,358 B2
(45) Date of Patent: Oct. 13, 2020

(54) CATHETER SYSTEM FOR SELECTIVELY MANIPULATING AND CONNECTING CARDIAC TISSUES

(71) Applicants: Lars Erickson, Newton, MA (US); Phoebe Erickson, Newton, MA (US); Michael R. Cole, Stratham, NH (US)

(72) Inventors: Lars Erickson, Newton, MA (US); Phoebe Erickson, Newton, MA (US); Michael R. Cole, Stratham, NH (US)

(73) Assignee: Lars Erickson, Newton, MA (US)

( * ) Notice: Subject to any disclaimer, the term of this patent is extended or adjusted under 35 U.S.C. 154(b) by 197 days.

(21) Appl. No.: 16/032,903

(22) Filed: Jul. 11, 2018

(65) Prior Publication Data

US 2019/0053904 A1 Feb. 21, 2019

Related U.S. Application Data

(63) Continuation-in-part of application No. 15/097,181, filed on Apr. 12, 2016, now Pat. No. 10,159,569.

(51) Int. Cl.
| | | |
|---|---|---|
| *A61F 2/24* | (2006.01) | |
| *A61B 17/32* | (2006.01) | |
| *A61B 17/3205* | (2006.01) | |
| *A61B 17/295* | (2006.01) | |
| *A61B 17/29* | (2006.01) | |
| *A61B 17/00* | (2006.01) | |

(52) U.S. Cl.
CPC .......... *A61F 2/2457* (2013.01); *A61B 17/295* (2013.01); *A61B 17/32* (2013.01); *A61B 17/32056* (2013.01); *A61F 2/2466* (2013.01); *A61B 2017/00243* (2013.01); *A61B 2017/00349* (2013.01); *A61B 2017/00783* (2013.01); *A61B 2017/294* (2013.01); *A61B 2017/2906* (2013.01); *A61B 2017/2931* (2013.01); *A61B 2017/2936* (2013.01); *A61B 2017/320044* (2013.01); *A61F 2220/0075* (2013.01); *A61F 2250/0007* (2013.01)

(58) Field of Classification Search
CPC ...... A61F 2/24; A61F 2/02; A61F 2/08; A61F 2/0805; A61B 17/00; A61B 17/04; A61B 17/08; A61B 17/122; A61B 17/32056; A61B 17/12; A61B 17/12004; A61B 17/12009; A61B 2017/00358; A61B 17/00234; A61B 2017/00225
See application file for complete search history.

(56) References Cited

U.S. PATENT DOCUMENTS

| | | |
|---|---|---|
| 4,576,165 A | 3/1986 | Green |
| 5,897,565 A | 4/1999 | Foster |
| 5,964,758 A | 10/1999 | Dresden |
| 6,352,503 B1 | 3/2002 | Matsui |
| 6,629,534 B1 | 7/2003 | Goldfarb |
| 6,610,072 B1 | 8/2003 | Christy |

(Continued)

*Primary Examiner* — George J Ulsh
(74) *Attorney, Agent, or Firm* — Bookstein IP Law

(57) ABSTRACT

A minimally invasive catheter and methods are provided for adjusting the chordae associated with an atrio-ventricular valve and for modifying the geometry of selected cardiac chambers. Clamps carried by the catheter are part of a prosthetic clamp assembly that includes the clamps and a cord attached to each of the clamps. The cord length can be adjusted after the clamps are attached to tissue. The clamps can be operated simultaneously or independently.

18 Claims, 12 Drawing Sheets

(56) References Cited

U.S. PATENT DOCUMENTS

| | | |
|---|---|---|
| 6,626,899 B2 | 9/2003 | Houser |
| 6,740,107 B2 | 5/2004 | Loeb |
| 6,752,813 B2 | 6/2004 | Goldfarb |
| 7,608,091 B2 | 10/2009 | Goldfarb |
| 7,635,386 B1 | 12/2009 | Gammie |
| 7,666,204 B2 | 2/2010 | Thornton |
| 7,704,269 B2 | 4/2010 | St. Goar |
| 7,758,596 B2 | 7/2010 | Mehmet |
| 7,998,151 B2 | 8/2011 | St. Goar |
| 8,147,542 B2 | 4/2012 | Maisano |
| 8,252,050 B2 | 4/2012 | Maisano |
| 8,292,884 B2 | 10/2012 | Levine |
| 8,500,800 B2 | 8/2013 | Maisano |
| 8,734,505 B2 | 5/2014 | Goldfarb |
| 8,778,016 B2 | 7/2014 | Janovsky |
| 8,790,394 B2 | 7/2014 | Miller |
| 8,852,213 B2 | 7/2014 | Gammie |
| 8,808,658 B2 | 8/2014 | Maisano |
| 8,888,844 B2 | 11/2014 | Eliassen |
| 8,894,705 B2 | 11/2014 | Eliassen |
| 8,956,406 B2 | 2/2015 | Subramanian |
| 8,961,597 B2 | 2/2015 | Subramanian |
| 8,992,606 B2 | 3/2015 | Ballarda |
| 9,011,515 B2 | 4/2015 | Schweich, Jr. |
| 9,044,246 B2 | 6/2015 | Goldfarb |
| 9,050,188 B2 | 6/2015 | Schweich, Jr. |
| 9,125,739 B2 | 9/2015 | Paniagua |
| 9,125,742 B2 | 9/2015 | Yoganathan |
| 9,155,622 B2 | 10/2015 | Ballarda |
| 9,161,837 B2 | 10/2015 | Kapadia |
| 9,005,279 B2 | 12/2015 | Gabbay |
| 9,198,757 B2 | 12/2015 | Schroeder |
| 9,232,995 B2 | 1/2016 | Kovalsky |
| 9,232,998 B2 | 1/2016 | Wilson |
| 9,232,999 B2 | 1/2016 | Maurer |
| 9,241,790 B2 | 1/2016 | Lane |
| 9,248,014 B2 | 2/2016 | Lane |
| 9,860,858 B2 | 1/2018 | Gou et al. |
| 2001/0049509 A1 | 12/2001 | Sekine |
| 2004/0193197 A1 | 9/2004 | Vidal |
| 2006/0095025 A1 | 5/2006 | Levine |
| 2007/0118151 A1 | 5/2007 | Davidson |
| 2007/0198038 A1* | 8/2007 | Cohen ................ A61B 17/0401 606/150 |
| 2007/0270643 A1 | 11/2007 | Lu |
| 2008/0255589 A1 | 10/2008 | Blakeney |
| 2009/0143639 A1 | 6/2009 | Stark |
| 2010/0023118 A1 | 1/2010 | Medlock |
| 2014/0114404 A1 | 4/2014 | Gammie |
| 2015/0150634 A1 | 6/2015 | Isoda |
| 2016/0015410 A1 | 1/2016 | Asirvatham |
| 2016/0213377 A1 | 7/2016 | Shankarsetty |
| 2017/0290663 A1 | 10/2017 | Erickson |
| 2019/0053904 A1 | 2/2019 | Erickson |

* cited by examiner

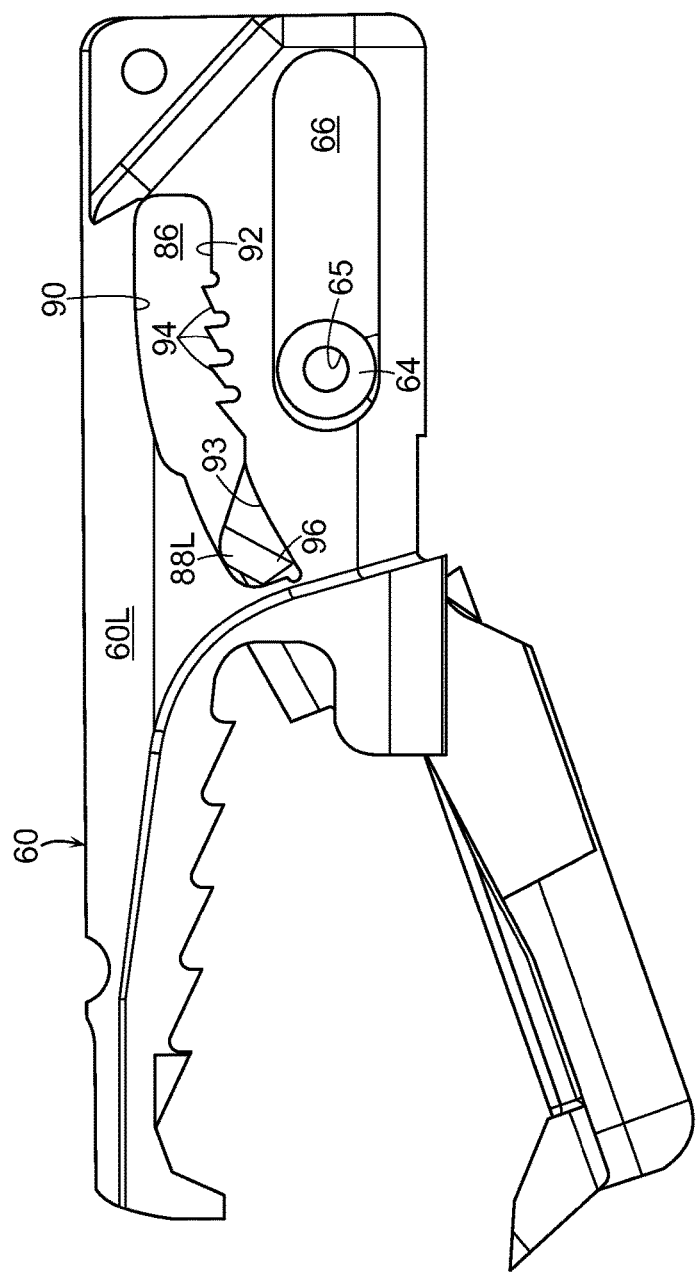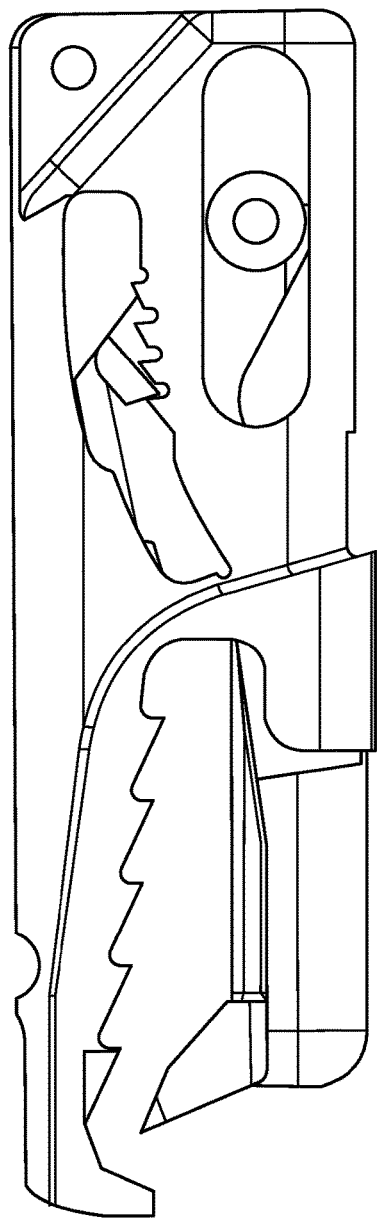
FIG. 13
FIG. 14

CATHETER SYSTEM FOR SELECTIVELY MANIPULATING AND CONNECTING CARDIAC TISSUES

FIELD OF INVENTION

The invention relates generally to minimally invasive devices and techniques for selectively manipulating and connecting cardiac tissues to treat cardiac anomalies and for adjusting the closing positions of the leaflets of a malfunctioning atrio-ventricular (A-V) valve by selectively adjusting the length of one or more chordae associated with the valve.

BACKGROUND

The heart has a left side and a right side, each side including an atrium and a ventricle. The atria receive blood returning through veins to the heart and the ventricles pump blood away from the heart, through arteries, to circulate blood through the body. The blood returns to the right side of the heart through the venous system. The heart also includes four one-way valves (aortic, pulmonary, mitral and tricuspid) that function to maintain unidirectional blood flow as the heart contracts in a pumping stroke (systole) and then relaxes and expands to fill the ventricles (diastole). Each side has an A-V valve (the tricuspid and mitral valves) that controls flow from its atrium to its associated ventricle, and each ventricle has an output valve (the pulmonary valve and aortic valve). When the heart muscle contracts (systole) blood is pumped from both ventricles through their respective output valves. Oxygenated blood from the left ventricle is pumped through the aortic valve to the aorta and branching arteries while blood from the right ventricle is pumped through the pulmonary valve to the lungs where it is oxygenated. The oxygenated blood from the lungs is returned to the heart and is received in the left atrium. During diastole, blood in each atrium is drawn through its associated A-V valve to refill its associated ventricle in readiness for the next cardiac contraction.

In a healthy, properly functioning heart the A-V valves close fully during systole to prevent backflow of blood from the ventricles to the atria as the ventricles contract. Each of the mitral and tricuspid valves is defined by an arrangement of leaflets flexibly attached to an annular supportive ring. The leaflets have free marginal edges that engage each other during systole to close the flow path between the atrium and its associated ventricle. The closed positions of the leaflets of the A-V valves are limited and defined by tendonous chordae that are attached, at one end, to papillary muscles in the lower portions of the ventricles and, at their upper ends, to the margins and undersides of the leaflets of the A-V valves as suggested in FIG. 2. In a healthy heart, the lengths of the chordae limit the movement of the leaflets during systole so that as the blood pressure in the ventricle increases, the free, marginal edges of the leaflets engage each other to close the valve and prevent backflow from the ventricles to the atria. During diastole the leaflets are not restrained by the chordae and their marginal edges are free to separate to allow blood flow from the atria to the associated ventricle.

Various cardiac-related diseases, however, may affect the heart by distorting its shape in ways that can impair heart function. Portions of the heart may become enlarged or portions may become weakened or displaced such that the heart does not function as it should. For example, in some conditions the leaflets of the mitral (left side) or tricuspid (right side) valve may not close properly and may result in backflow during systole. Deformation in the shape or structure of the heart wall may effect a shift in the relative position of the papillary muscles to which the chordae are attached. That, in turn, affects the positions of the valve leaflets, tethering them so that they may not close fully during systole. For example, such heart muscle deformation may occur in patients with coronary artery disease or those who have had myocardial infarction (heart attack). In addition, patients with myxomatous valve disease, such as mitral valve prolapse, may have abnormally long chordae that do not hold the leaflet margins in a closed position during systole. Patients with chordae that functionally too short (tethered) or too long are prone to developing mitral valve regurgitation which may result in reduced cardiac efficiency. That, in turn, may lead to further cardiac complications such as enlargement of the atria and/or ventricles, pulmonary hypertension, heart failure and other problems.

Various procedures and techniques have been employed and proposed to compensate for deformation in the heart structure by surgically reforming the heart geometry, including the use of prostheses to aid in such adjustment. See, for example, U.S. published patent applications 2007/0265658 (Nelson) and 2008/0312492 (Jayaraman). Valve repair may involve, for example, complex, invasive, open-heart surgery to surgically repair the valve, as by reforming or reinforcing the shape of the annulus of the valve or by selectively attaching portions of the marginal edges of leaflets together. Other remedies may involve replacement of an A-V valve with a mechanical valve or a bioprosthetic valve. Less invasive, catheter-based procedures also have been proposed, including adjustment of the chordae of the mitral or tricuspid valve. It is among the objects of the invention to provide catheter-based devices to facilitate minimally invasive adjustment of cardiac geometries and structures by selectively connecting and positioning regions or components of the heart in a manner that compensates for cardiac anomalies.

SUMMARY

In order to adjust the heart geometry by attaching selected portions of the heart to each other, a catheter is provided with a clamp assembly that includes a pair of tissue clamps or anchors connected to each other by a cord or tether. The length of the tether is selected so that when the clamps are anchored to selected portions of the heart they will define a selected relative position of the tethered portions. By placement of one or more of such clamp assemblies, the heart may be reshaped or reconfigured to alleviate the anomaly. The catheter is adapted to be advanced through a patient's vasculature to place the distal end of the catheter within the chamber of the heart where the clamp assembly is to be deployed. The catheterization procedure should be done in conjunction with imaging technology, for example, ultrasound, trans-esophageal echocardiography, intracardiac echocardiography, fluoroscopy, angioscopy, catheter based magnetic resonance imaging, computed tomography and the like. The imaging technique may enable visualization of blood flow and particularly how the placement of the clamp assembly affects heart function. If the cardiac anomaly has not been adequately corrected the procedure can be repeated to make further adjustments until the desired result is achieved.

In the case of adjusting the length of one or more chordae, a chord may be severed or folded to a hairpin shape and its ends or folded portions can be connected with a clamp assembly having a cord of a length to increase or decrease the effective length of the native chord, as described in U.S. patent application Ser. No. 15/097,181, filed Apr. 12, 2016, the disclosure of which is incorporated herein by reference. The prosthetic clamp assembly is carried at the distal end of the catheter. The clamps are spaced laterally on opposite sides of the central axis of the catheter at diametrically opposite positions on the catheter and are open in a distal direction in order to receive a chord or other tissue oriented transversely to the axis of the catheter. The length of the prosthetic cord is selected to correspond to the degree of adjustment to be made to the natural chord. The catheter also may include a snare that can be extended axially between the clamps and beyond the distal end of the catheter to engage a selected natural chord. The snare and engaged chord then can be retracted to draw that chord into the open jaws of the clamps. The clamps then are caused to close to clamp the natural chord and a severing element carried by the catheter then may be operated to sever the natural chord between the clamps. The clamps then are released from the catheter. Upon release, the effective length of the selected chord will have been adjusted in an amount determined by the length of the prosthetic clamp assembly. The catheter then may be withdrawn. Should it be desirable to lengthen (or shorten) additional of the chordae another catheter may be introduced or the original catheter may be reloaded with another clamp assembly. In another illustrative embodiment, the length of the prosthetic cord that connects the clamps can be adjusted after the clamps have been securely attached to tissue. As used herein, the term "chord" refers to the cardiac components that connects the A-V valves to a portion of a ventricle wall and the term "cord" refers to the prosthetic tethering element that connects the clamps to each other.

The invention also may be employed to adjust the geometry of portions of the heart walls that may have been weakened and/or dilated as a result of any of a number of various cardiac deficiencies. To that end, the clamps of the clamp assembly can be placed and activated individually, separately from each other, so that the clamps can be anchored to selected portions of the interior of the heart wall. The clamps can be placed so that the length of the assembly positions the walls of the heart in a desired, modified geometry. For example, the device may be used to connect a papillary muscle to another portion of the heart wall to reorient the position of the papillary muscle to affect valve function. In another example the device may be used to grip regions of the heart wall to connect them to modify the geometry of a heart chamber. The device may include an arrangement by which the cord length can be adjusted after the clamps have been anchored to tissue to draw the connected tissue portions toward each other.

Thus, the invention provides catheter-based methods to increase or decrease the effective length of one or more chordae to restore the ability of an associated A-V valve to close and reduce or prevent back flow and to correct anomalies in cardiac geometries. As used herein, the term "effective length" is intended to mean the length of a natural chord as modified by use of the invention. Ideally "effective length" would be an adjusted length that would enable the associated A-V valve leaflets to coapt during systole without backflow or to reshape the geometry of selected cardiac chambers to remedy cardiac insufficiencies.

THE DRAWINGS

The various objects and advantages of the invention will be appreciated more fully from the following detailed description with reference to the accompanying drawings in which:

FIG. 13 is an enlarged side view of a clamp with jaws configured to grip a selected portion of a wall of a heart chamber, with the lower jaw in its most forward, open position;

FIG. 14 is an illustration of the clamp of FIG. 13 with the lower jaw in its fully retracted, closed and locked position;

DETAILED DESCRIPTION

Figure 1:
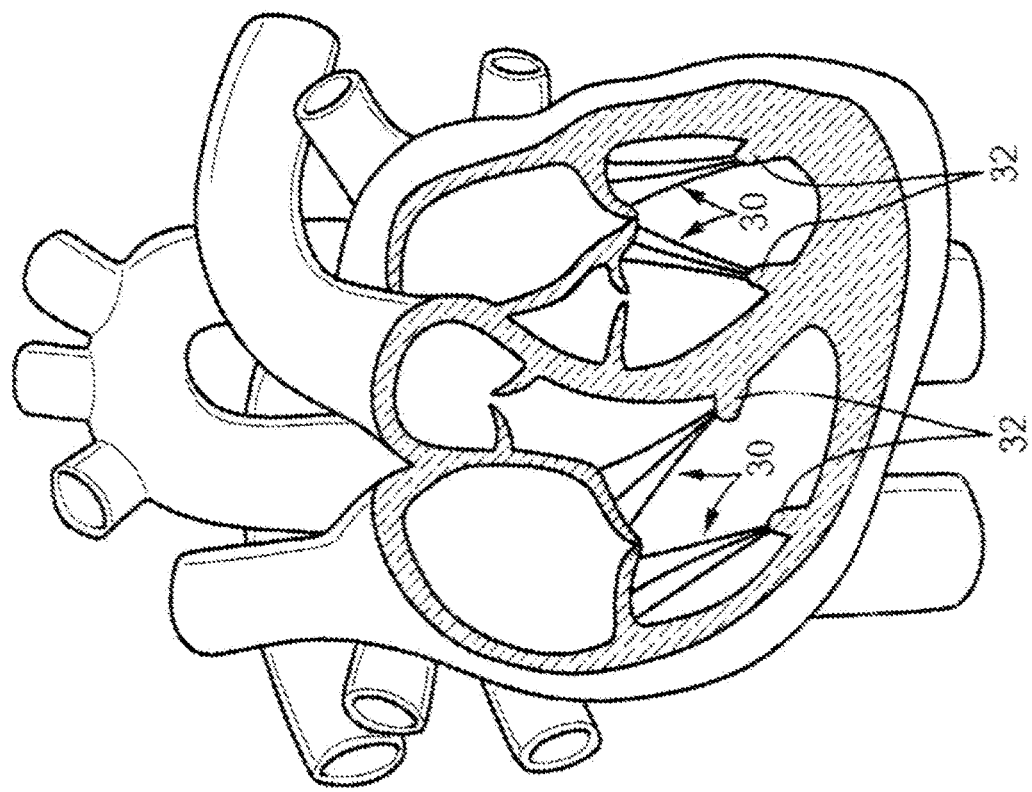
FIG. 1 is a diagrammatic sectional illustration of a heart showing the right and left sides and the four valves that control the direction of blood flow.

FIG. 1 shows the anatomy of the heart and the direction of blood flow. The heart has a left side 10 and a right side 12, the sides being separated by a septum 14. The left side, which provides the primary pumping function, includes a left atrium 16 that receives oxygenated blood returning to the heart from the lungs and a left ventricle 18 that receives oxygenated blood from the left atrium 16. The left atrium 16 and left ventricle 18 are separated by the mitral valve 20 that, when functioning normally, permits flow in one direction, from the atrium 16 to the ventricle 18 and to the arteries, as indicated by the arrows.

The right side 12 of the heart, which receives return blood and directs it to the lungs, includes the right atrium 22, the right ventricle 24 and a tricuspid valve 26 between the right atrium and right ventricle. The right atrium receives blood returning to the heart through the venous system 28 and blood flows from the right atrium 22 to the right ventricle 24 through the tricuspid valve 26. When functioning normally, the tricuspid valve 26 permits flow in only one direction, from the right atrium 22 to the right ventricle 24.

Figure 2:
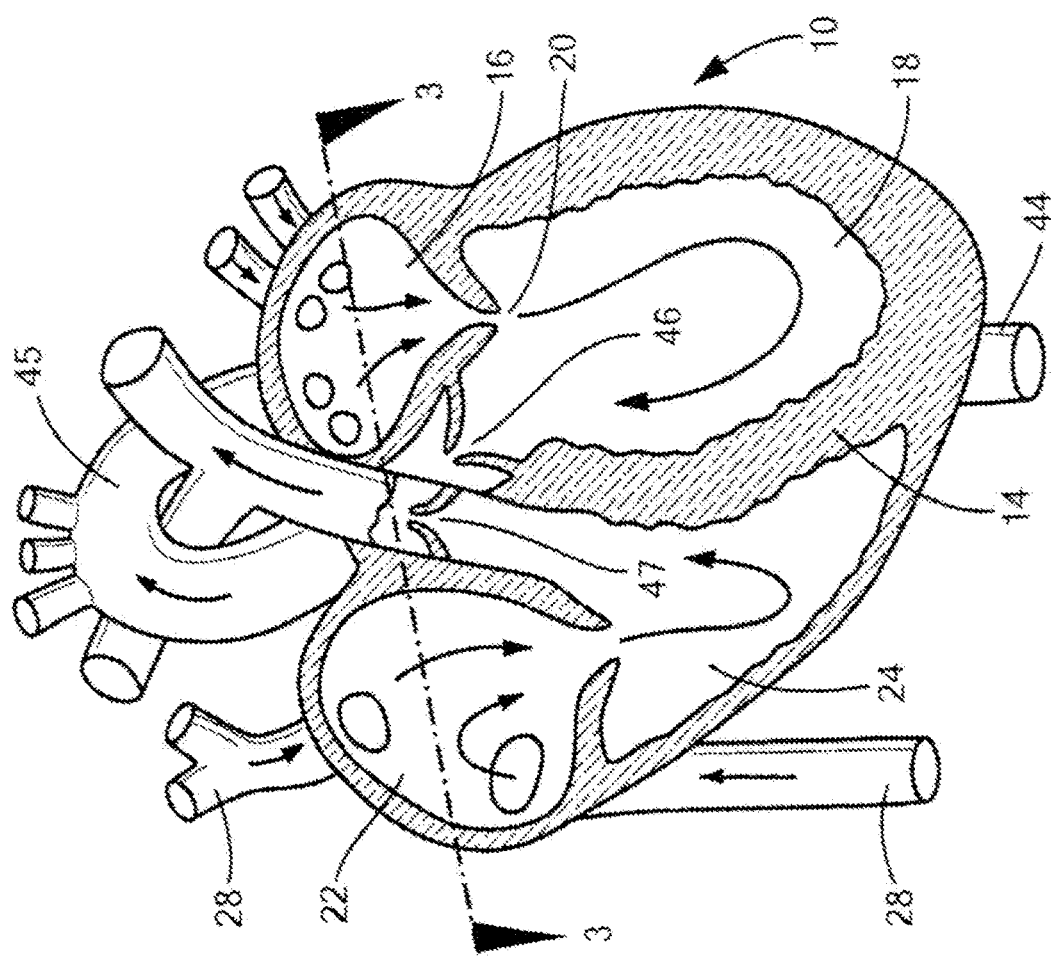
FIG. 2 is a diagrammatic, cut-away of a heart illustrating the arrangement of chordae and their associated atrio-ventricular valves.
Figure 3:
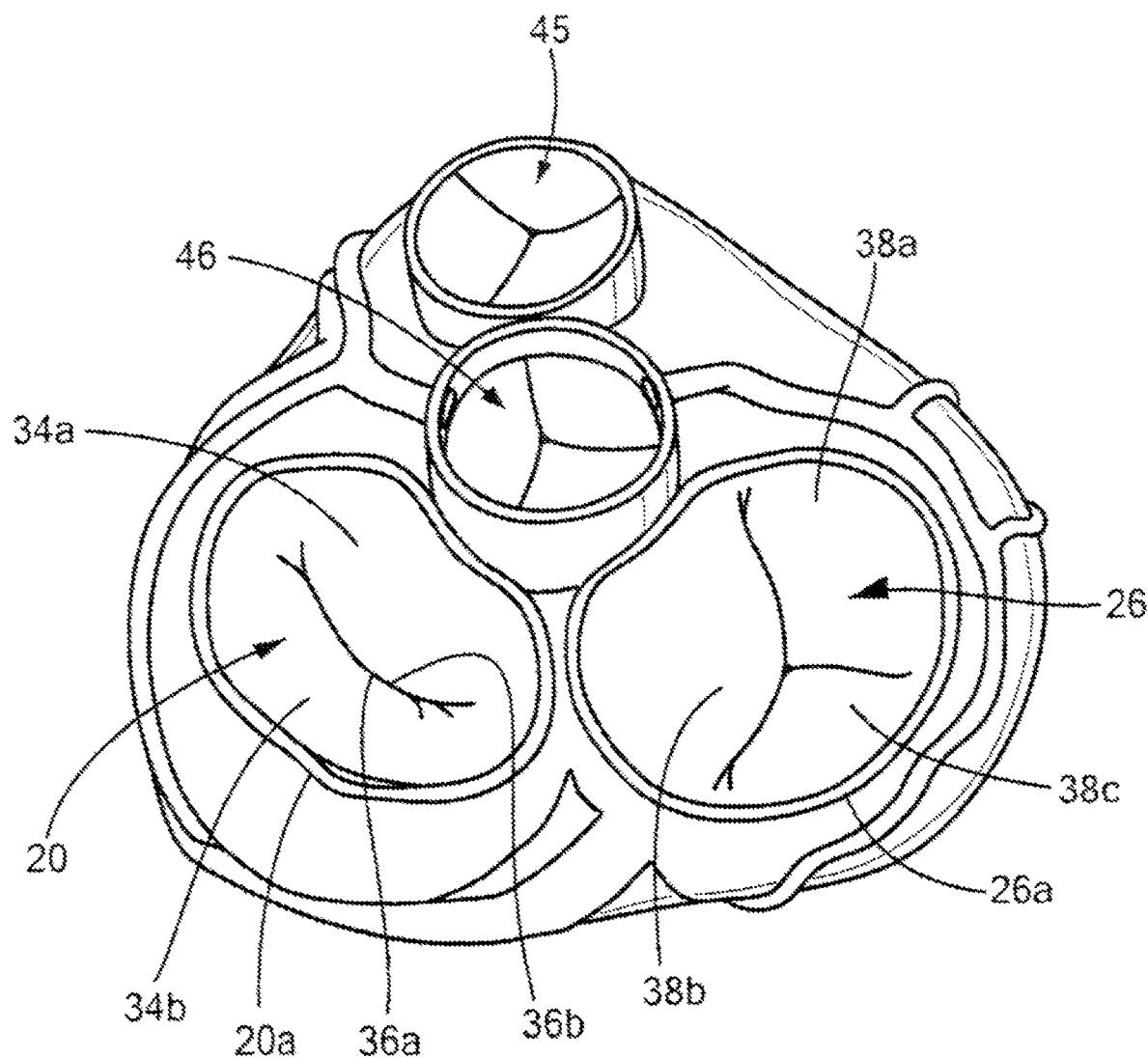
FIG. 3 is a diagrammatic plan sectional view of the heart as seen along the line 3-3 of FIG. 1 and showing the arrangement of the four cardiac valves with all of the valve leaflets closed to show how their marginal edges coapt when closed.

The structure of each of the A-V valves includes leaflets that open freely in response to pressure differential developed during diastole, as the heart expands from its contracted state. The leaflets of the mitral valve 20 are attached flexibly to an annular ring 20a and the leaflets of the tricuspid valve are attached to another annular ring 26a. The mitral valve 20 has two semilunar leaflets including an anterior leaflet 34a and a posterior leaflet 34p as seen in FIG. 3. In a healthy heart the marginal edges 36a, 36b of the leaflets 34a, 34b coapt to close the valve during systole and open during diastole. In an impaired heart the leaflets may not close properly resulting in valve regurgitation or prolapse. The tricuspid valve 26 of the right side of the heart has three leaflets 38a, 38b, and 38c with associated chordae 30, functions similarly to the mitral valve, and is subject to similar malfunction. During systole, the extent of leaflet movement is restrained by a number of tendon-like chordae arranged in a parachute-like array (shown diagrammatically at 30 in FIG. 2) in each ventricle that extend from a papillary muscle 32 at the interior of the ventricle wall to the underside or margins of the leaflets that define the associated A-V valve. In a healthy heart, the chordae 30 limit the movement of the leaflets so that the marginal free edges of the leaflets coapt as shown in FIGS. 2 and 3. However, in the case of a heart with impaired function the shape of the heart may become altered such that one or more of the chordae no longer allow the leaflets to close properly, resulting in backflow of blood from the ventricle to the atrium during systole. Backflow results in a reduced ejection fraction and reduced pumping efficiency. Other variations in heart geometry may impair heart function and may be correctible by drawing selected portions of the heart toward each other with the present invention.

A malfunctioning A-V valve may be corrected by a procedure to shorten or lengthen the effective length of selected of the chordae associated with that valve so that the marginal edges of the valve leaflets coapt during systole (see the aforementioned patent application Ser. No. 15/097,181) or to connect internal regions of the heart walls to reshape the heart chambers depending on the condition and anatomy of a particular patient. The geometry of the heart can be reshaped to correct anomalies and to add prosthetic cords by connecting, selectively, internal portions of the heart to adjust their relative positions and geometries. These advantages may be achieved in a relatively minimally-invasive approach with the catheter of the present invention.

Figure 4:
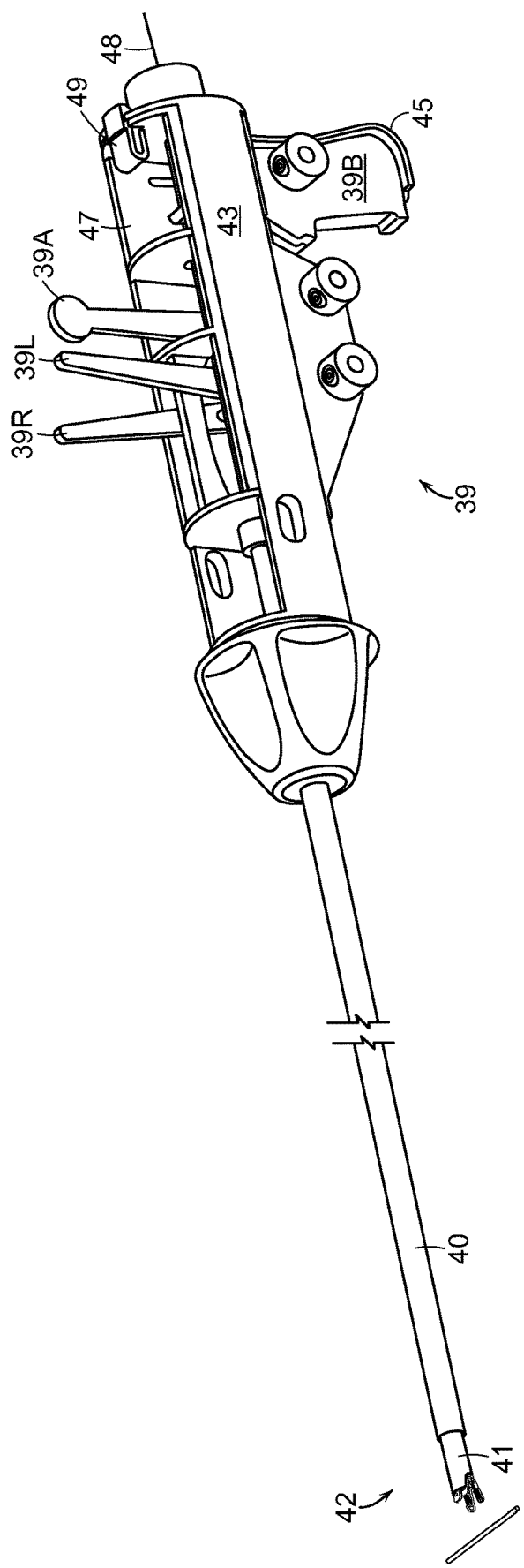
FIG. 4 is a fragmented illustration of a device embodying the invention and including a control handle at the proximal end of the device.
Figure 5:
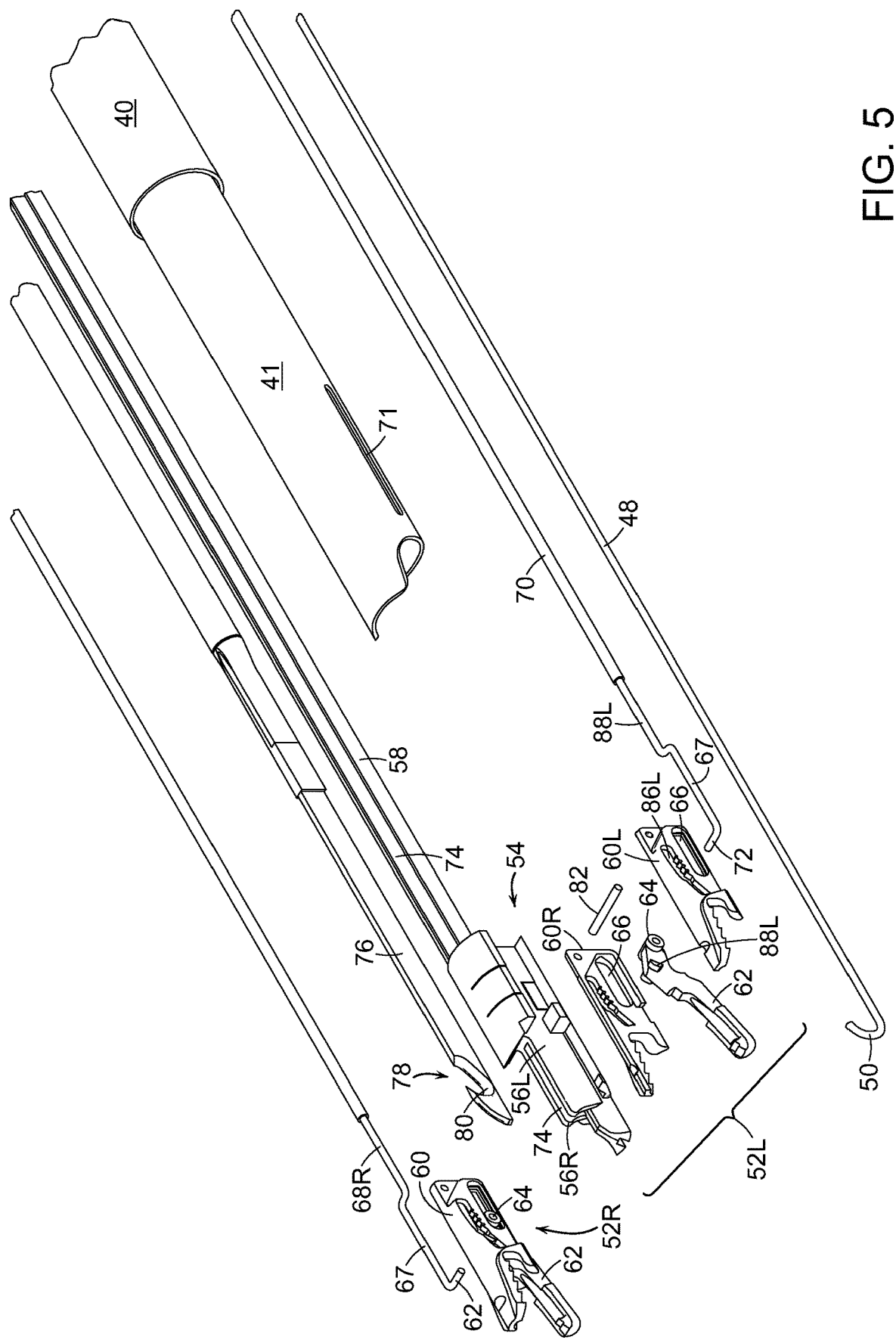
FIG. 5 is an exploded illustration of the device.

FIGS. 4 and 5 illustrate an embodiment of a catheter as may be employed in the practice of the invention, for example, to adjust the effective length of one or more chords 30 sufficiently to limit the closure of its associated valve leaflets so that the margins of the leaflets coapt properly during systole or to connect internal regions of the heart walls to reshape the heart chambers depending on the conditions and anatomy of a particular patient. In an illustrative embodiment of the invention the catheter may include an elongate, flexible outer sheath 40 and an inner coaxial sheath 41 slidably disposed in the central lumen of the outer sheath 40. The catheter has proximal and distal ends and may include a control handle 39 at the proximal end with controls 39L, 39R, 39A and trigger 39B to control operation of the instrumentalities at the distal end (FIG. 4). In the illustrative embodiment, the control handle 39 may include an outer body 43 with an attached pistol grip 45 and an inner body 47 that is slidably disposed within the outer body 43 but is held in fixed position, as by a removable clip 49, until the end of the procedure, as described below. The outer sheath 40 is attached, at its proximal end, to the outer body 43 of the handle 39 and the inner sheath 41 is attached, at its proximal end, to the inner body 47 of the handle 39. Relative movement of the sheaths 40, 41 is effected by moving the handle bodies 43, 47.

The catheter components may be constructed from a variety of materials commonly used in catheters and should be dimensioned in association with the selection of materials to be advanceable through the patient's cardiovascular system. The catheter may be advanced by any of numerous, well-known approaches to place and position the distal end 42 of a catheter within a heart chamber (e.g., ventricle 18, 24) to be treated, as will be appreciated by those skilled in the art. For example, to reach the left side 10 of the heart to treat a malfunctioning mitral valve 20, the catheter may be advanced through a guide catheter (not shown) retrograde from a percutaneous puncture in the femoral artery, through the aorta 44 and aortic valve 46 and into the left ventricle 18. This can be performed while the heart is beating and avoids the complexities of placing the patient on extracorporeal support such as a heart-lung machine, as would be the case in open-heart surgery. Typically, a guiding catheter (not shown) and associated guide wires (not shown) may be employed using well known techniques (e.g., Seldinger) to guide the catheter through the aorta 44, aortic arch and aortic valve 46 into the left atrium 16 and then through the mitral valve 20 into the left ventricle 18. The inner sheath 41 may be provided with one or more lumens to receive guide wires, facilitate flushing, injection of contrast agent and the like. Other approaches to reach the left ventricle 18 also may be employed including access from the right side 12 of the heart and through the septum 14 or access through the apex 48 of the heart. The invention may be used to repair the function of a mitral or tricuspid valve, as well as to modify the geometry of cardiac chambers.

Procedures with the invention are best performed under visualization, as described above, so that the clinician can determine and control the position of the distal end 42 of the catheter as well as the valve leaflets 36a, 36p and associated chordae 30 as well as to visualize blood flow through the valve and cardiac chambers and whether and to what degree backflow or other insufficiency is present.

FIG. 5 illustrates the components of the catheter. In addition to the inner and outer sheaths 41, 40, the catheter includes a snare 48 that can be extended distally beyond the distal end 42 of the catheter to engage a chord and draw the chord proximally into the open jaws of a pair of clamps, described below. The snare may be in the form of an elongate wire with a distal end formed to define a hook 50. The hook preferably is flexible but of sufficient stiffness to engage and manipulate a chord and may be formed, for example, from a nitinol alloy. The snare can be slidably contained in a longitudinally extending slot (not shown) formed along the underside of the inner sheath 41 and is maintained in the slot by the overlying outer sheath 40. The proximal end of the snare 48 can extend out of the proximal end of the handle and can be manipulated by the clinician to be extended, retracted and rotated. The wire snare can be removed by pulling it proximally through the handle, the hooked distal end of the snare being sufficiently flexible for that purpose.

The catheter also carries a pair of clamps 52L, 52R each of which is adapted to engage and anchor to tissue such as chords or internal regions of the cardiac walls. The clamps 52L, 52R are operable independently of each other but can be operated simultaneously. In FIG. 5, the left clamp 52L (as seen from the proximal end of the device) is shown in exploded view while the right clamp 52R is shown as assembled. The clamps 52L, 52R may be maintained in the catheter in a partially open initial position receptive to a chord or other cardiac tissue. The clamps 52L, 52R are supported within the catheter by a chassis 54 having opposing sides 56 L, 56R that are formed to receive the clamps 52L, 52R, respectively. The chassis 54 is connected to an elongate control shaft 58 that extends proximally where it is connected to a control in the handle 39, such as a trigger 39B, to enable the chassis to be extended distally beyond the ends of the sheaths 40, 41 to facilitate separation of the clamps from the delivery device at the end of the procedure. The clamps 52L, 52R are releasably mounted to the chassis 54 as described below.

The clamps 52L, 52R may be as small as about three to four millimeters long, made from a biocompatible material and may be formed by 3-D printing. Each clamp may include an upper jaw 60 and a lower jaw 62, shown separately in FIG. 6. The upper jaw 60 may be formed in two mirror-image halves 60L, 60R (FIG. 5) that are joined after the lower jaw 62 has been positioned between them. The lower jaw 62 is slidable and pivotable relative to the upper jaw 60 and has pivot bearings 64 formed on each side of the proximal end of the lower jaw 62, the bearings being slidably received in longitudinal slots 66 formed in each of the halves 60L, 60R of the assembled upper jaw 60. A transverse aperture 65 is formed through each pivot bearing 64. The lower jaws 62 of the clamps 52L, 52R are separately movable by longitudinally extending control rods 68L, 68R connected at their proximal ends to controls 39L, 39R on the handle and at their distal ends to the lower jaws 62. The distal tips 72 of the control rods 68L, 68R are bent inwardly and are received in the respective apertures 65 in the pivot bearings 64. As a lower jaw is advanced or retracted by movement of a control rod 68L, 68R, the lower jaw also pivots about the pivot bearings 64 to open or close by a camming arrangement 86, 88 that cooperates with the positioning of the pivot bearings, as described below.

Each of the control rods may be slidably retained in a tubular sheath 70 that, in turn, extends through the inner sheath 41. A distal segment 67 of each control rod may be shaped to extend radially outward of the axis of the catheter in order to maintain the diameter of the inner sheath 41 at a minimum. The inner sheath may be provided with elongated slots 71 to receive the segments 67 of the control rod and to allow the distal portions 67 of the control rods 68 to spring radially outwardly when released, as described below.

Figure 11:
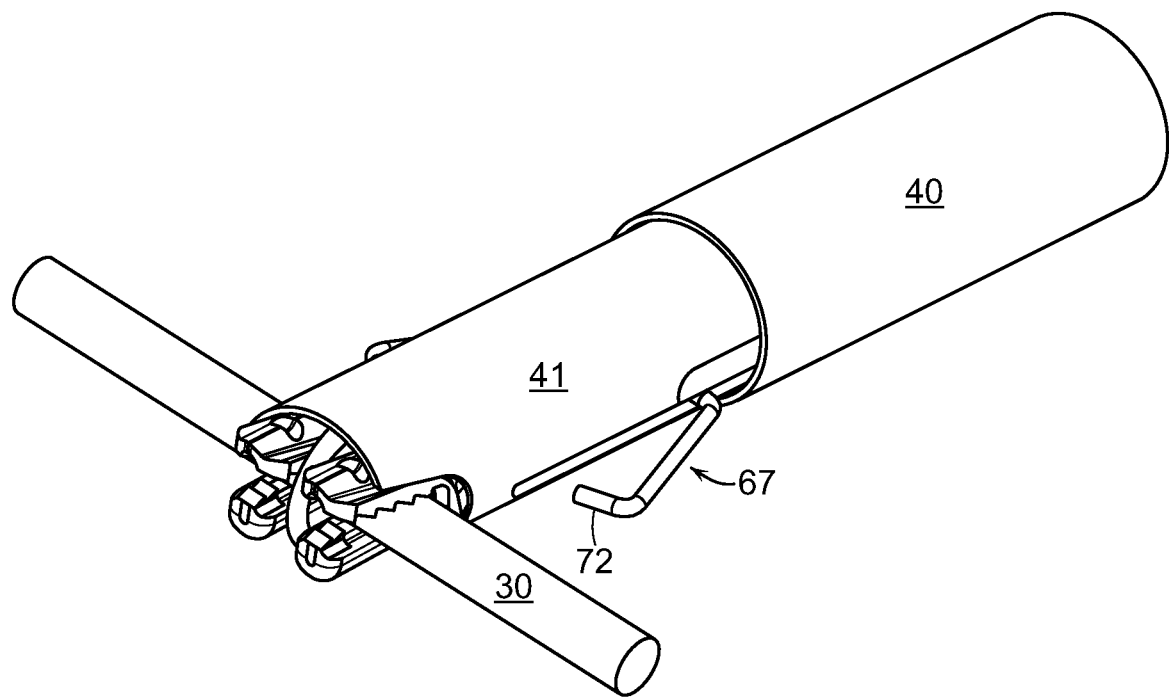
FIG. 11 is an illustration of the device after the chord has been cut and the outer sheath has been withdrawn to release the clamps.

The distal portions of the control rods are formed to be resiliently biased toward a transverse, radially outward configuration so that they will detach from the pivot bearings, as illustrated in FIG. 11 when the outer sheath 40 is retracted. The control rods 68L, 68R are connected to the clamps 52L, 52R during the positioning of the distal end of the catheter within the heart and are allowed to spring apart to disengage the distal tips 72 and release the clamps only after tissue has been securely clamped and the device is to be released from the catheter. The distal portions of the control rods are maintained in their radially inward positions by the outer sheath 40 that overlies the slots 71 when the sheath 40 is in its forward position. The control rods are released by proximal retraction of the outer sheath 40 to allow the distal portions of the control rods to spring outwardly through the slots 71 causing the tips 72 to disengage from the clamps. So released, the clamps then are free to separate from the chassis 54 after the inner sheath 41 is retracted relative to the chassis, as described below.

When the catheter is adapted for use in adjusting the length of a native chord it may be provided with a cutting blade to cut the native chord. To that end, in the illustrative embodiment, chassis control shaft 58 may be formed to have a channel 74 that is receptive to a cutter shaft 76. The cutter shaft is 76 has a proximal end that is connected to a handle control 39A and a distal end that includes a cutting blade 78. The distal tip of the cutting shaft 76 is blunt and preferably is curved and smooth so that it can slide past tissue easily. A rearwardly facing hooked cutting edge 80 is formed on the distal tip and is oriented so that the cutting edge cuts tissue only when the cutting shaft is moved in a proximal direction. During the procedure to adjust the length of a native chord the cutter shaft 76 is projected distally past the chord to hook the chord and then is drawn proximally to sever the chord.

The clamps 52L, 52R are connected by a prosthetic cord 82 and together form a prosthetic clamp assembly 84 (FIG. 17) that may be used to reconnect the severed portions of a natural chord, for example, to increase the effective length of that chord. The prosthetic cord may be formed from any suitable durable biocompatible material such as, for example, expanded polytetrafluoroethylene (EPTFE). The clamps 52L, 52R are carried at the distal end of the catheter by the chassis 54 in diametrically spaced relation with the prosthetic cord 82 being folded and disposed within the catheter body as shown and described in patent application Ser. No. 15/097,181. The clamps are arranged so that they are on opposite sides of the catheter axis and embrace the snare 48 which is movable between the clamps. The clamps may be initially configured in the catheter in a partially open configuration so that they may receive a transversely oriented natural chord 30 that has been engaged by and drawn proximally by the snare 48. The clamps preferably may have teeth 73 or other irregular surfaces formed on the inner faces of the clamp legs, with the teeth having edges arranged to be oriented transversely to a chord, leaflet margin or other tissue engaged within the clamp. When the clamps are intended to engage and grip internally facing walls of the heart, the jaws may be provided with teeth configured to so engage the heart walls, as described below.

Figure 6:
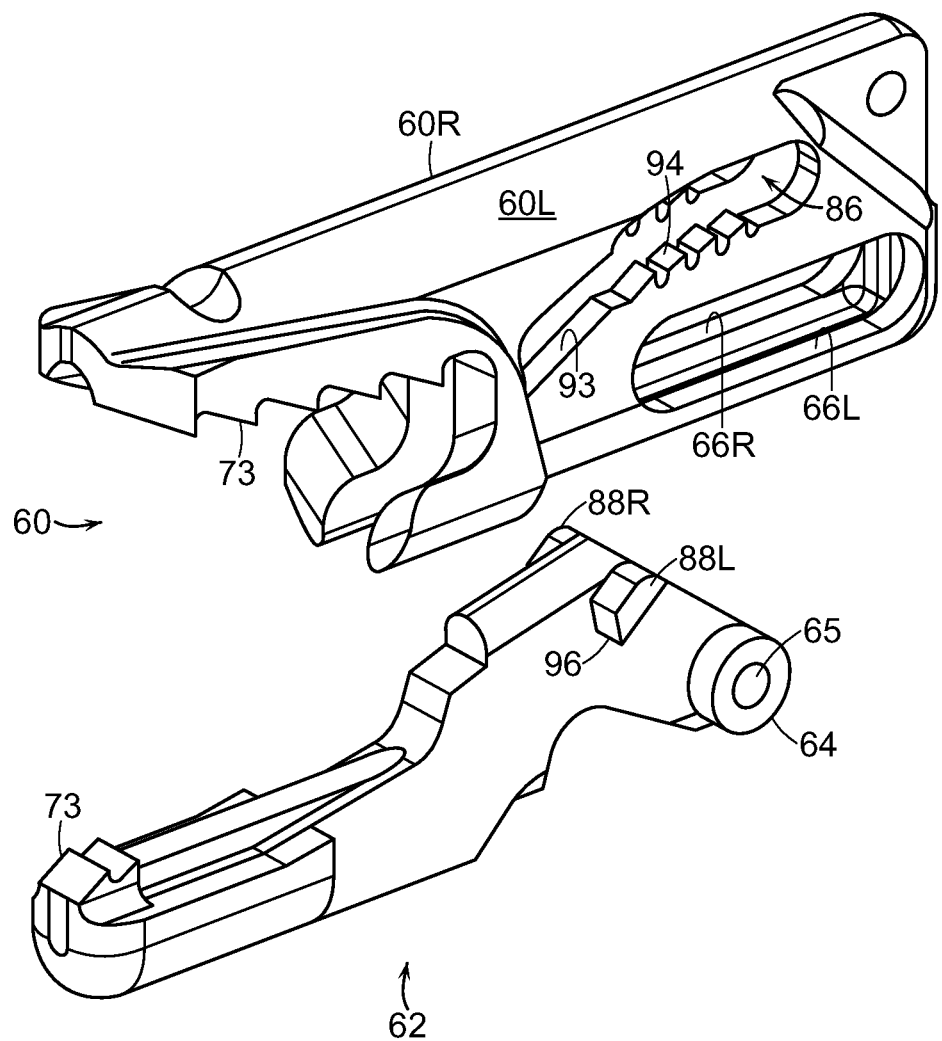
FIG. 6 is an isometric illustration of the jaws, shown separately for ease of description.
Figure 7:
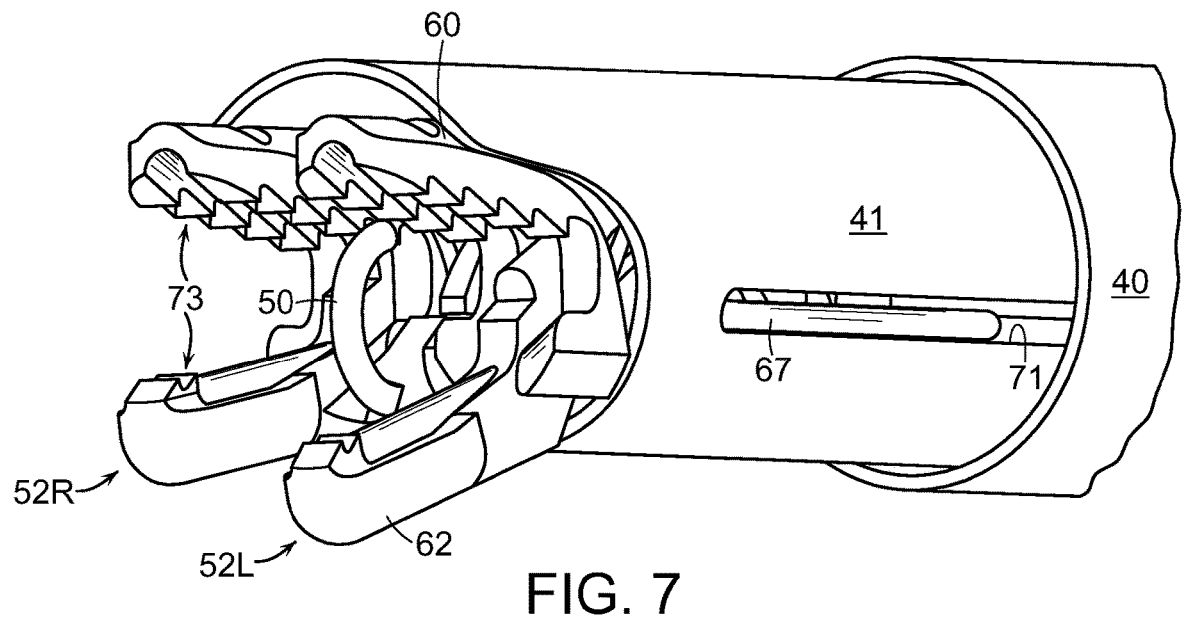
FIG. 7 is an illustration of the distal end of the catheter with the jaws partly open in a configuration in readiness to be navigated into a patient.
Figure 10:
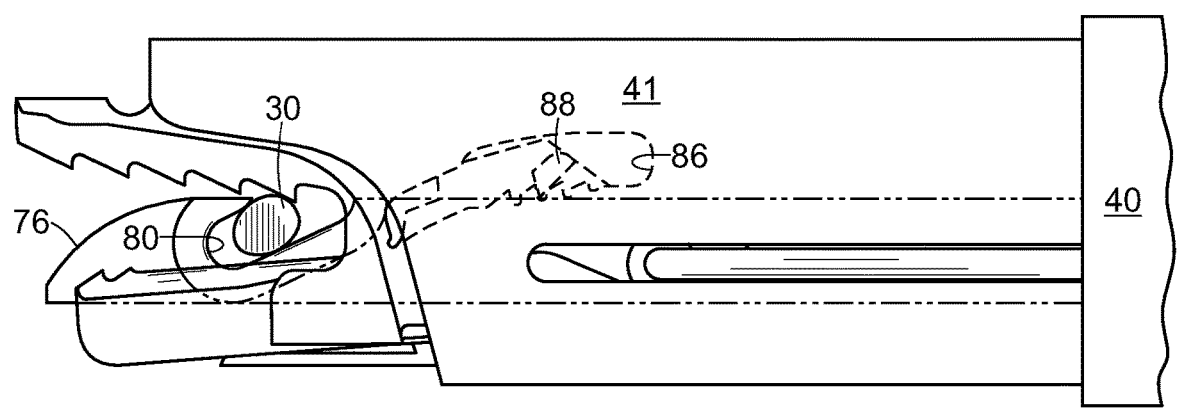
FIG. 10 is an illustration similar to FIG. 8 of the distal end of the catheter of one embodiment of the invention showing the chord engaged by the snare and the cutter blade and with the clamp jaws retracted and closed on the chord.
Figure 12:
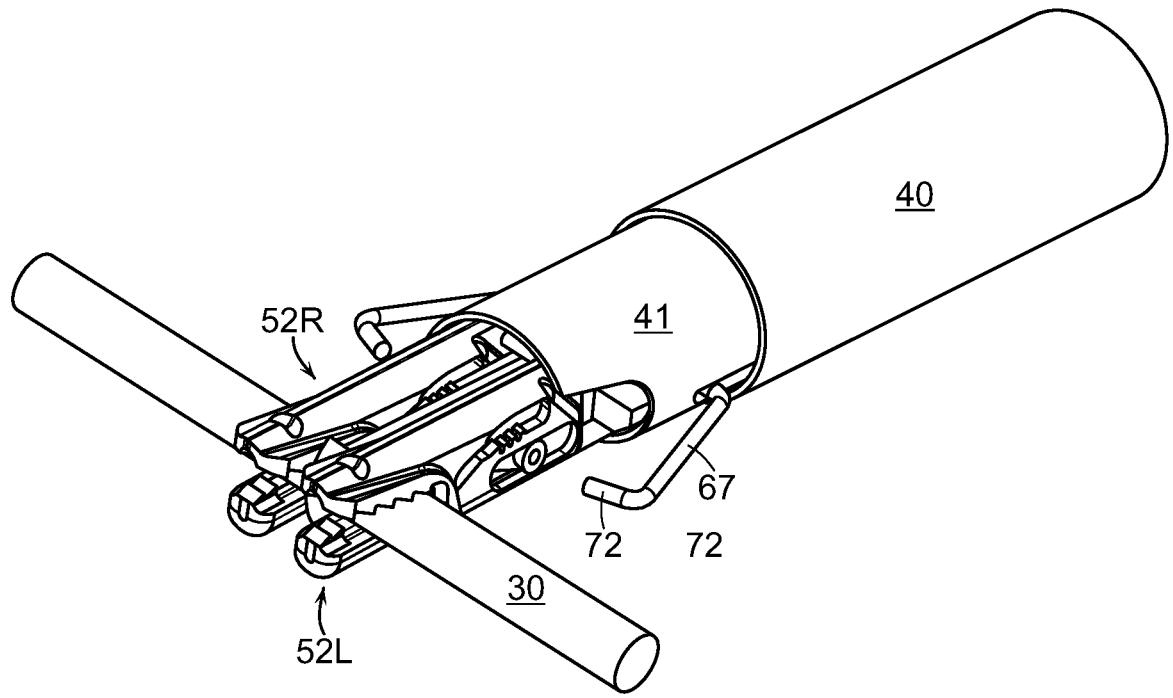
FIG. 12 is an illustration of the connector and attached chord segments after the inner sheath has been withdrawn relative to the chassis to facilitate separation of the clamp assembly from the catheter.

As shown most clearly in FIG. 6 and enlarged FIG. 12, each upper jaw half 60L, 60R of each upper jaw 60 has a longitudinally extending camming slot 86L, 86R, respectively, arranged to receive transversely extending cams 88L, 88R formed on a proximal portion of the lower jaw 62, forwardly of the pivot bearings 64. Each camming slot has an upper edge 90 and a lower edge 92, with the lower edge 92 having a smooth forward portion 93 and a rearward portion having a plurality of teeth 94. The slots 86L, 86R and the cams 88L, 88R are configured to cooperate to guide the lower jaw from an initial, partially open, position intermediate the positions of FIGS. 12 and 13, to the more open position (FIG. 12) better to receive a chord 30 or tissue and, after selected tissue has been engaged, to close the lower jaw 62 to grip the tissue between the jaws and to lock the jaws in a tissue-gripping position (FIG. 10). Each cam has an edge 96 that engages the lower edge 92 of the slot 86 and, when the lower jaw is retracted proximally, causes the lower jaw 62 to pivot upwardly and rearwardly to the more closed position. In the intermediate position, the cam edge 96 is in contact with the rearward region of the smooth forward portion 93. With tissue gripped between the jaws, the lower edge of the cam follower 96 engages one of the teeth 94 formed along the proximal portion of the lower edge 92 of the camming slot 86 so that the lower jaw is prevented from opening and releasing the gripped tissue. Each lower jaws is movable independently of the other by manipulation of its associate handle control 39L, 39R by which the control rods 86 are advanced or retracted.

It should be noted that in each of the illustrated embodiments, the rearward portions of the clamps are similarly constructed; the clamps differ only in their structure at the forward ends of their jaws. Thus, in FIGS. 4 and 5, the forward, distal ends of the jaws have tooth configurations adapted to engage chordae while in FIGS. 12 and 13 the tooth configurations are more aggressive in that the teeth of both jaws project forwardly to engage and dig into the tissue walls so that when they close they can establish a firm grip on the tissue. FIGS. 16A-16D illustrate an intermediate configuration in which the teeth at the distal ends of the jaws may be used both for capturing chordae as well as gripping tissue walls.

Figure 8:
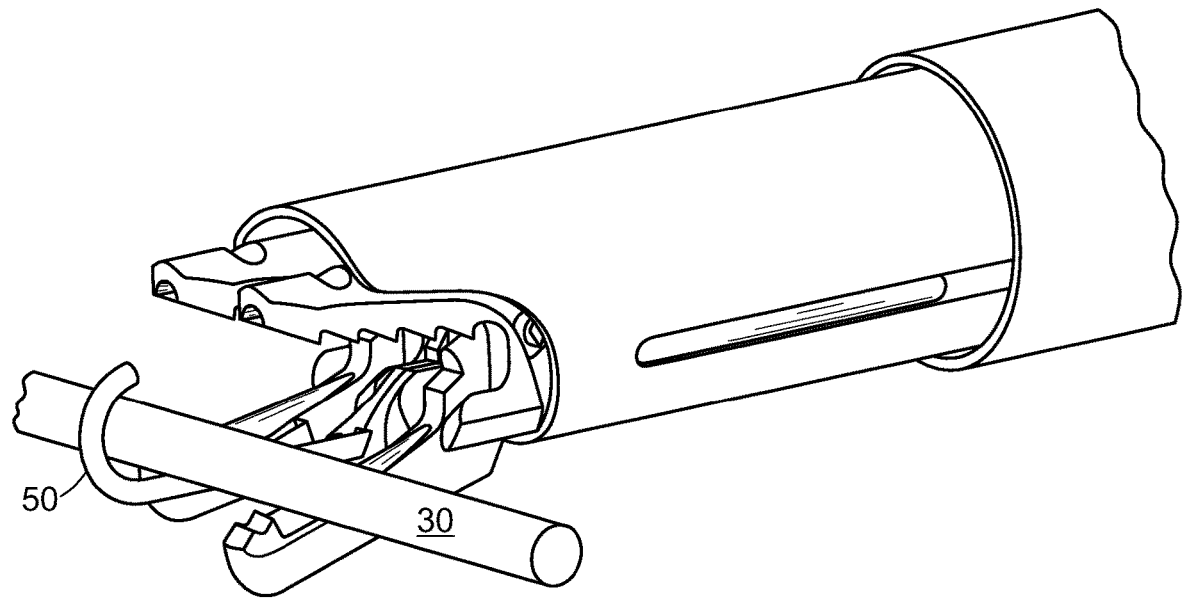
FIG. 8 is an illustration similar to FIG. 7 with the snare extended distally to engage a chord.
Figure 9:
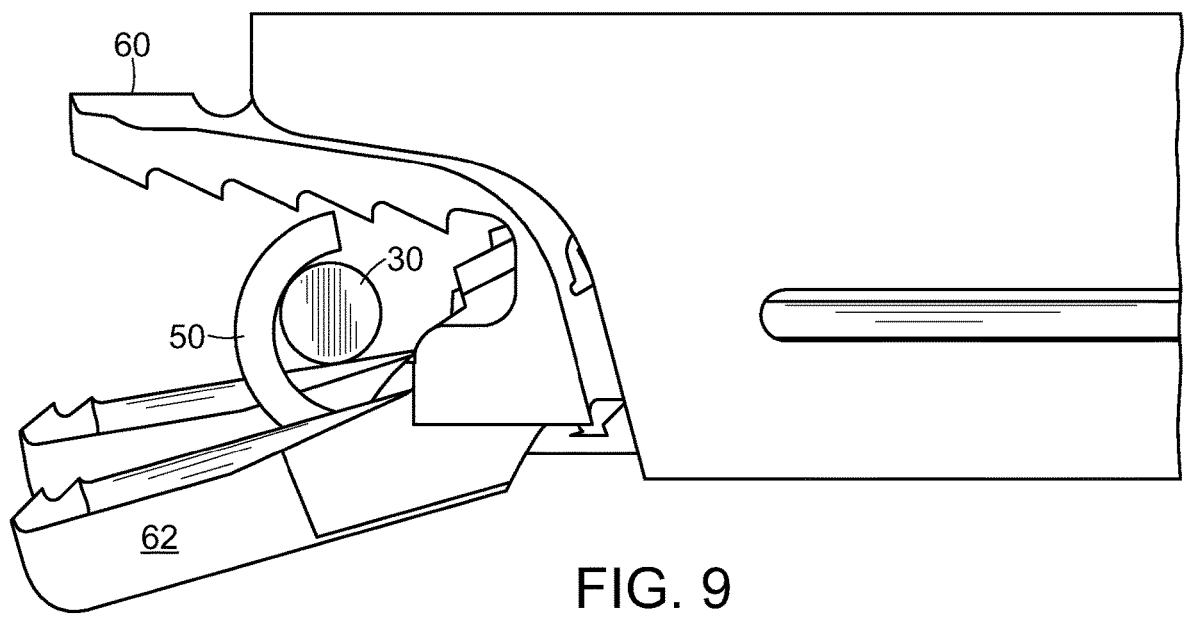
FIG. 9 is a side view of the distal end of the catheter with the snare retracted to draw the chord into the jaws of the clamps.
Figure 17:
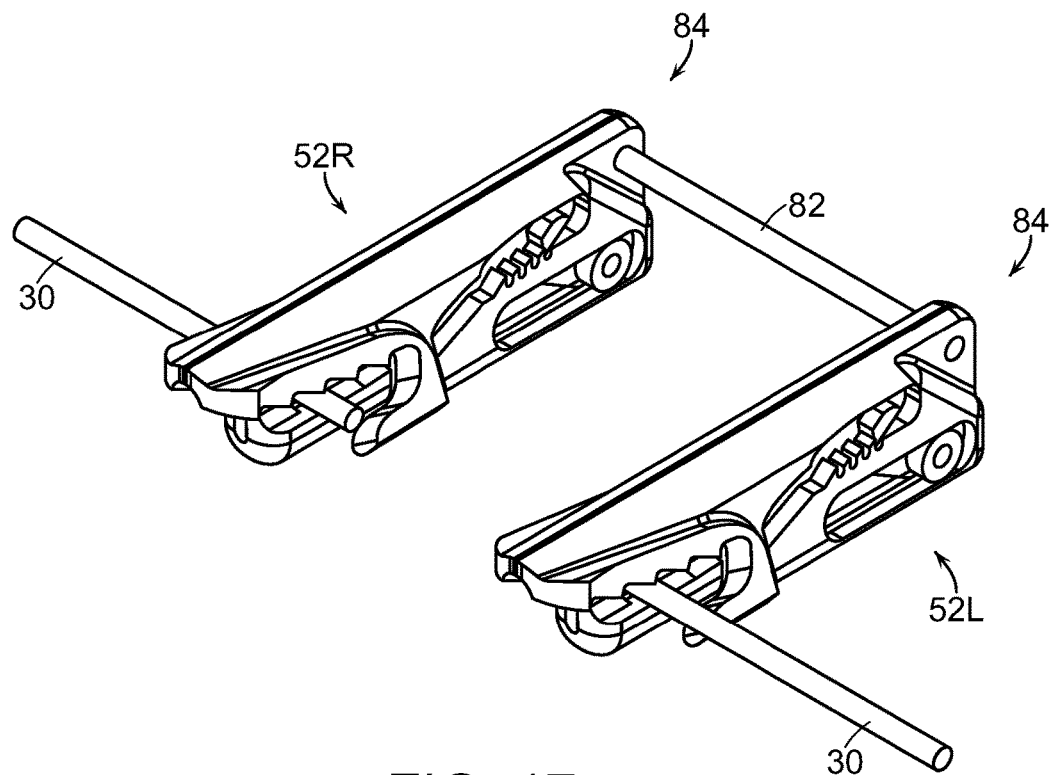
FIG. 17 is an illustration of a clamp assembly and effectively lengthened chord, released from the catheter.

When using the device to adjust the length of a native chord to correct the functioning of a valve, the distal end of the catheter is advanced into the ventricle with the clamps 52L, 52R in their initial, intermediate positions. With the distal end of the catheter positioned to receive a chord in the clamps, the lower jaws of the clamps may be urged forwardly by manipulation of the handle controls 39L, 39R, to fully open the jaws (FIGS. 8 and 12) and the snare 48 may be extended (FIG. 8) to engage the selected chord 30 and then retracted proximally to draw the chord into the open clamps (FIG. 9). The lower jaws then are moved proximally by manipulation of the handle controls 39L, 39R and control rods 68, causing the lower jaw to pivot upwardly and move rearwardly toward the upper jaw as guided by the cams 88 and camming slots 86. With the clamps securely attached to a selected natural chord 30, the cutting blade 78 is advanced distally until the chord is engaged within the hook of the blade 78 and then is drawn proximally to cause cutting edge 80 to sever the selected chord between the clamps so that when the prosthetic clamp assembly 84, comprised of the two prosthetic clamps 52R, 52L and the connecting cord 82 (FIG. 17), is released from the catheter the effective length of that chord will be increased by an amount dependent on the length of the prosthetic clamp assembly 84 (FIG. 17). The prosthetic clamp assembly then may be released from the catheter by retracting the outer sheath to free the distal portions of the control rods so that the distal ends 72 can spring out of engagement with the pivot bearings. The chassis then can be extended beyond the inner sheath by operating the trigger 39B (or the inner sheath can be retracted from about the chassis) to fully expose the clamps and enable them to separate from the chassis (FIGS. 12 and 17). The length of the prosthetic clamp assembly 84 should be selected to modify the effective length of the chord 30 so that the marginal edges of the valve leaflets will coapt during systole. The clinician may perform the procedure with several chordae, as is deemed appropriate by the clinician to restore proper functioning of the valve leaflets.

Figure 15A:
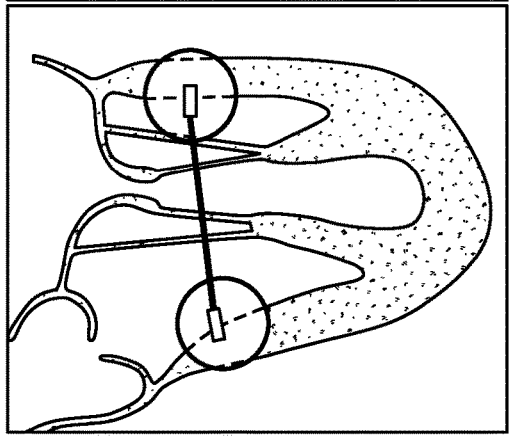
FIGS. 15A-15G are diagrammatic cross sectional illustrations of the manner in which portions of a left ventricle of a mammalian heart can be connected by the clamp assembly of the invention.
Figure 15B:
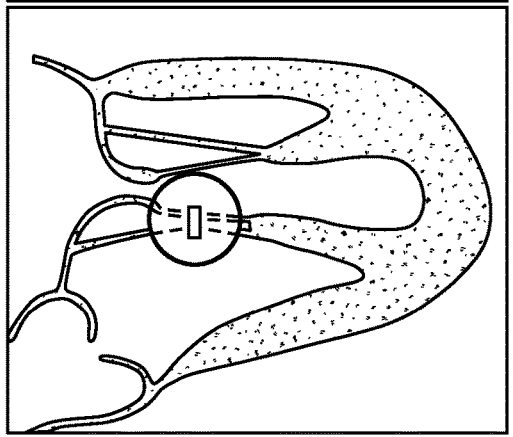
Figure 15C:
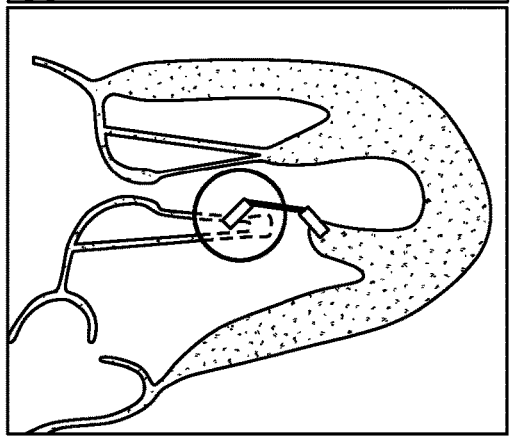
Figure 15D:
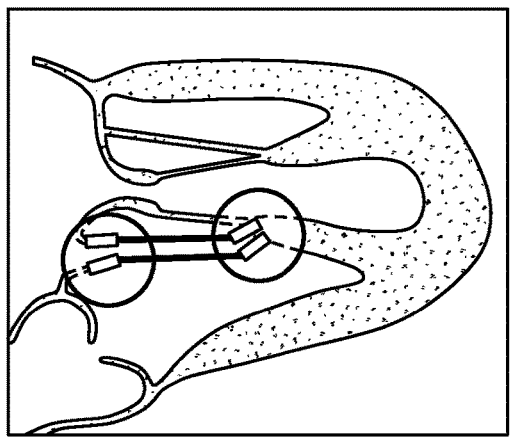
Figure 15E:
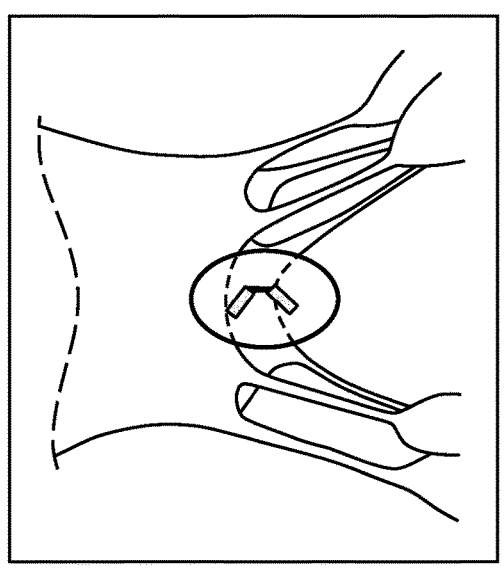
Figure 15F:
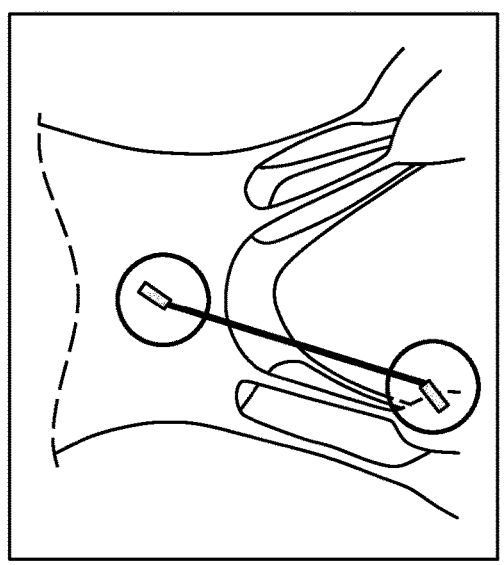
Figure 15G:
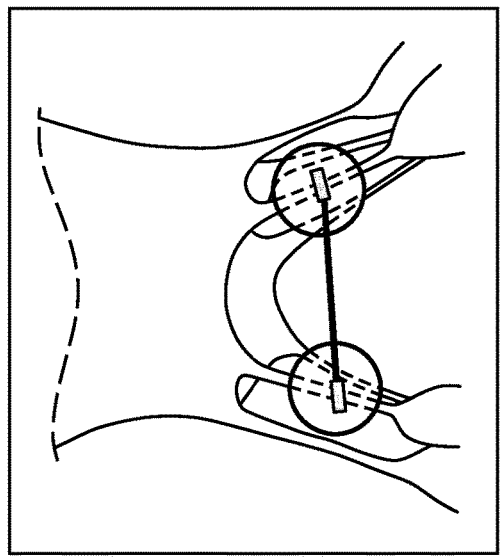
Figure 16A:
FIGS. 16A-16D are side view and isometric illustrations of another clamp configuration in open and closed positions.
Figure 16B:
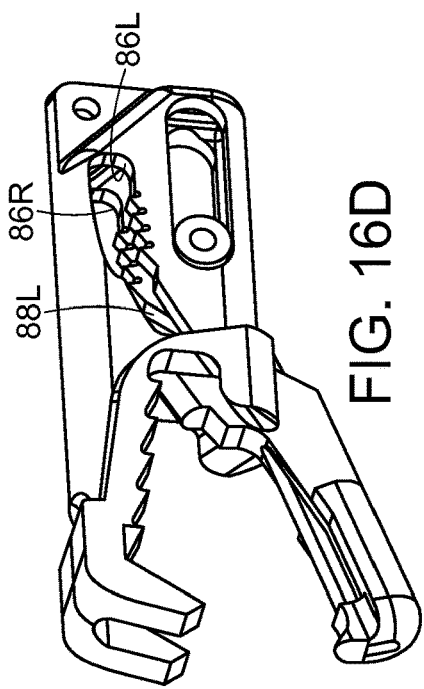
Figure 16C:
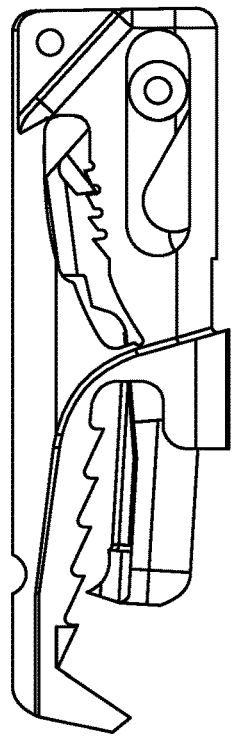
Figure 16D:
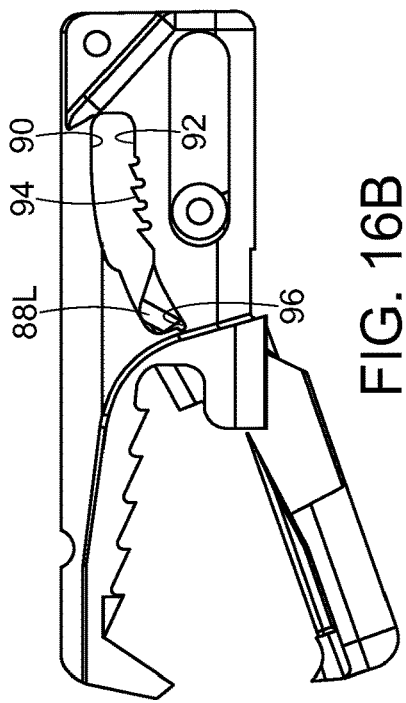
Figure 18:
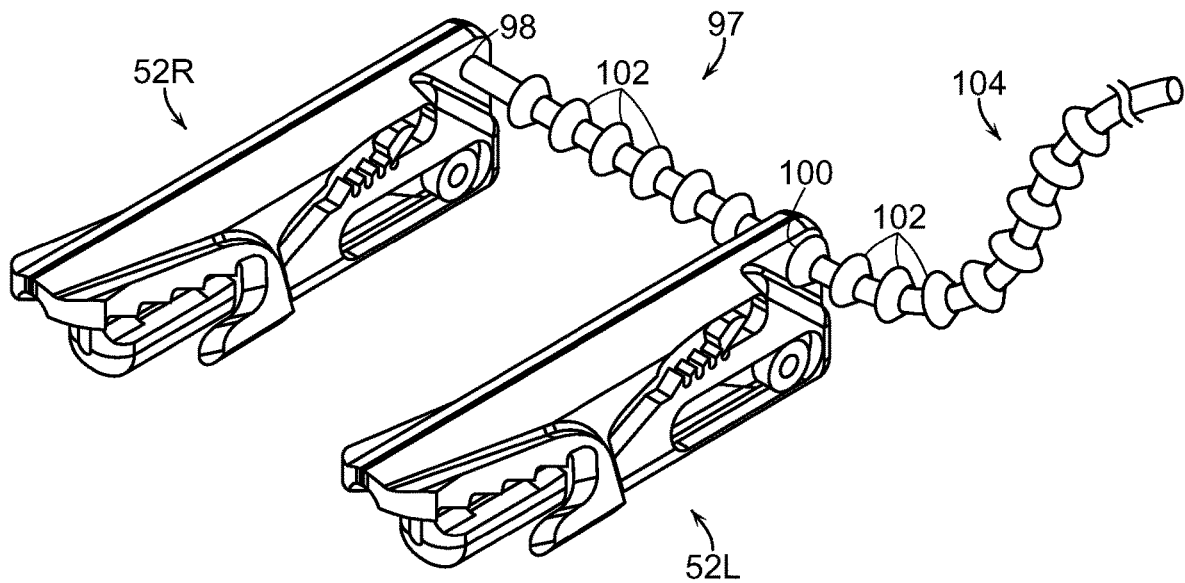
FIG. 18 is a somewhat diagrammatic illustration of a clamp assembly in which the length of cord connecting the clamps can be adjusted after the clamps have been clamped to tissue.

FIGS. 15A-15G illustrate, diagrammatically, some examples of the manner in which the invention may be employed to adjust the geometry and configuration of cardiac anatomy. FIG. 15A illustrates the manner in which opposite walls of a ventricle may be brought closer together by using a clamp assembly with a desired length of cord, then first anchoring one of the clamps to a first region of the ventricular wall and then, after the first clamp is securely attached, anchoring the other clamp to an opposing region of the ventricular wall, the cord length having been selected to effect the desired degree of separation between the selected portions of the walls. FIG. 15B illustrates an individual clamp used to tie two or more native chordae together. FIG. 15C illustrates reattachment of native chordae to a detached papillary muscle. FIG. 15D shows the device attaching the margins of the leaflets of a mitral valve to a papillary muscle. FIG. 15E illustrates attachment of a papillary muscle to a portion of a mitral valve leaflet at a location other than the marginal edge. FIG. 15F illustrates attachment of a chord associated with one papillary muscle attached to a chord of another papillary muscle.

FIG. 17 illustrates another aspect of the invention in which the length of the cord connecting the clamps 52L, 52R may be adjusted after the clamps have been attached to tissue. In that embodiment the cord 97 is attached securely, as at 98, at the proximal end of one of the clamps (e.g., 52R). The other end of the cord is passed through an opening 100 in the other of the clamps (e.g., 52L) and the cord is provided with a plurality of stops 102 along its length. The stops 102 and the opening 100 are configured to allow the tail portion 104 of the cord 97 to be passed through the opening 100 only in a direction that will shorten the length of cord extending between the clamps 52L, 52R. For example, the cord and opening 100 may be formed to be similar to adjustable zip-ties or cable ties. The tail 104 of the cord can pass through the catheter to the proximal end of the catheter where it can be pulled through the opening 100 to achieve the desired length between the clamps, thereby achieving a desired distance between connected portion of the cardiac anatomy. The tail portion 104 of the cord then can be severed by manipulating cutter shaft 76 to position the cutting edge 80 of the blade 78 adjacent the tail 104 and operating the cutter shaft to sever the tail 104. The snare may be used to facilitate positioning the tail 104 to be cut. The severed tail then can be removed from the patient.

It should be understood that in the foregoing description and the following claims, terms such as proximal, distal, forward, rearward, upward, downward, upper and lower are intended as relative directions or positions to indicate the relative positions or directional movements of the components of the invention.

From the foregoing, it should be appreciated that the invention provides a minimally invasive approach to correcting the geometry of cardiac components as well as providing devices and techniques to treat mitral and tricuspid valve insufficiency. It should be understood, however, that the foregoing description is intended merely to be illustrative and that other modifications and equivalents may be apparent without departing from the principles of the invention.

The invention claimed is:

1. A catheter for selectively connecting and adjusting the geometry of a mammalian heart, comprising:
   an elongate catheter shaft having proximal and distal ends and a longitudinally extending axis;
   an anchoring assembly releasably carried at the distal end of the catheter shaft, the anchoring assembly comprising a cord having a pair of tissue anchors attached to the cord, the tissue anchors being disposed at and carried at the distal end of the catheter in transversely spaced relation to and on opposite sides of the axis, each anchor having distally facing portions adapted to engage, dig into and become anchored in a cardiac wall without fully penetrating through the cardiac wall, each anchor being operable separately and independently of the other, each anchor being releasable from the catheter after being anchored in a cardiac wall.

2. The catheter as defined in claim 1 wherein the length of the cord between the anchors is adjustable.

3. The catheter as defined in claim 2 wherein the cord is attached to one of the anchors and is received through an opening in the other of the anchors, the cord and opening being configured to allow passage of the cord through the opening in a direction that reduces the distance between the connected anchors whereby the distance between anchors can be adjusted.

4. The catheter as defined in claim 3 further comprising a cutting element, adapted to cut a tail portion of the cord that protrudes out of the opening.

5. The catheter as defined in claim 4 further comprising a snare adapted to engage and draw a chord or the cord proximally to a position where it can be cut by the cutting element.

6. The apparatus as defined in claim 1 further comprising:
a cutting element moveable longitudinally between the anchors.

7. The catheter as defined in claim 6 wherein the cutting element has a blunt distally facing end and a proximally facing cutting edge whereby the cutting element can be extended beyond a selected element within the heart and then retracted proximally to effect a cutting action of the element.

8. A catheter for selectively connecting and adjusting the position of cardiac tissues, the catheter having an elongate shaft having an axis with proximal and distal ends and comprising:
a clamp assembly comprising a pair of clamps releasably carried at the distal end of the catheter shaft, the clamps being disposed in transversely spaced relation and on opposite sides of the axis, each clamp having distally facing portions adapted to receive a selected, cardiac tissue, the clamps being closeable to securely grip selected tissue received within the clamps, each clamp being operable separately and independently of the other;
the clamp assembly having a prosthetic cord segment connected to each of the clamps;
each clamp comprising a first jaw having forward and rearward ends and having tissue gripping surfaces along a forward portion, and a second jaw having forward and rearward ends and having tissue gripping surfaces along a forward portion;
the rearward portion of each first jaw having a slot, extending in a forward-rearward direction;
the rearward portion of each second jaw having a pivot bearing slidably and pivotably received in the slot of the first jaw;
one of the jaws having a camming slot and the other of the jaws having a cam follower received in the camming slot, the calming slot and cam follower being configured to open or close the jaws as the pivot bearing is moved along the slot;
the rear portion of the camming slot having detents engageable with the cam follower so that when the second jaw has been retracted to grip tissue between the jaws the cam will engage a detent to lock the clamp in its tissue-clamping position.

9. The catheter as defined in claim 8 further comprising:
a cutting element moveable longitudinally between the clamps.

10. The catheter as defined in claim 9 wherein the cutting element has a blunt distally facing end and a proximally facing cutting edge whereby the cutting element can be extended beyond selected tissue and then retracted proximally to effect a cutting action.

11. The catheter as defined in claim 10 wherein the cutting element is in the form of a hook having a proximally facing opening.

12. The catheter as defined in claim 8 further comprising:
the catheter having a snare movably carried by the catheter, the snare adapted to engage tissue and draw engaged tissue proximally into the clamps.

13. The catheter as defined in claim 8 further comprising:
a chassis disposed at the distal end of the catheter, the chassis being adapted to releasably support the clamps on opposite sides of the chassis;
the catheter having an outer sheath and an inner sheath slidably contained within the outer sheath, each of the sheaths having a proximal position and a distal position relative to the chassis, the sheaths when in their distal positions overlying the rearward portions of the clamps when the clamps are mounted on the chassis, the inner and outer sheaths being separately retractable relative to the chassis from their distal positions to their proximal positions;
a pair of longitudinally movable control rods extending through the inner sheath, each control rod being associated with one of the clamps and having a distal portion that includes a radially inward extending distal tip that is received in an aperture in the pivot bearing of its associated clamp whereby longitudinal movement of the control rods can move the second jaws to open or closed positions;
the distal portion of each of the control rods being biased radially outward to disengage the tip from the pivot bearing;
the inner sheath having a pair of elongate slots that overlie the distal portions of the control rods to enable the distal portions of the control rods to protrude radially outwardly of the inner sheath;
the outer sheath, when in its distal position, overlying the slots on the inner sheath to contain the distal portions of the control rods and maintain the tips of the control rods in engagement with the pivot bearings, and when in its retracted, proximal position, exposes the slots sufficiently to allow the distal portions of the rods to spring apart to release the pivot bearings.

14. The catheter as defined in claim 4 further comprising:
the inner sheath being retractable relative to the chassis after retraction of the outer sheath to more fully expose the clamps to allow them to separate from the chassis.

15. The catheter as defined in claim 8 further comprising:
the gripping surfaces of the jaws being adapted to grip chordae.

16. The catheter as defined in claim 8 further comprising:
the gripping surfaces of the jaws being adapted to grip the wall of a cardiac chamber.

17. The catheter as defined in claim 8 further comprising:
the gripping surfaces of the jaws being adapted to grip leaflet tissue.

18. The catheter as defined in claim 8 wherein the prosthetic cord is attached to one of the clamps and is received through an opening in the other of the clamps, the cord and opening being configured to allow passage of the cord through the opening in a direction that reduces the distance between the connected clamps, whereby the distance between the clamps can be adjusted.

* * * * *